United States Patent
Moen et al.

(10) Patent No.: US 10,604,803 B2
(45) Date of Patent: Mar. 31, 2020

(54) TEST FOR PREDICTING THE ABILITY OF A SALMONID TO UTILISE DIETARY PIGMENT

(71) Applicant: Aquagen AS, Trondheim (NO)

(72) Inventors: Thomas Moen, Aas (NO); Jacob Seilo Torgersen, As (NO)

(73) Assignee: AQUAGEN AS, Trondheim (NO)

( * ) Notice: Subject to any disclaimer, the term of this patent is extended or adjusted under 35 U.S.C. 154(b) by 0 days.

(21) Appl. No.: 16/063,056

(22) PCT Filed: Dec. 16, 2016

(86) PCT No.: PCT/GB2016/053963
§ 371 (c)(1),
(2) Date: Jun. 15, 2018

(87) PCT Pub. No.: WO2017/103607
PCT Pub. Date: Jun. 22, 2017

(65) Prior Publication Data
US 2019/0002976 A1    Jan. 3, 2019

(30) Foreign Application Priority Data

Dec. 16, 2015 (GB) .................................. 1522230.0

(51) Int. Cl.
*C12Q 1/6876* (2018.01)
*C12N 9/22* (2006.01)
*C12N 15/11* (2006.01)

(52) U.S. Cl.
CPC ............. *C12Q 1/6876* (2013.01); *C12N 9/22* (2013.01); *C12N 15/11* (2013.01); *C12Q 2600/124* (2013.01); *C12Q 2600/156* (2013.01)

(58) Field of Classification Search
None
See application file for complete search history.

(56) References Cited

U.S. PATENT DOCUMENTS 9,920,368 B2 * 3/2018 Moen .................. C12Q 1/6888

FOREIGN PATENT DOCUMENTS

| CN | 104543449 | 4/2015 |
| WO | 2015/189617 | 12/2015 |

OTHER PUBLICATIONS

NCBI Database search for ss# 1960972623, available via URL:. <ncbi.nlm.nih.gov/search/all/?term=ss1960972624> and <nlm.nih.gov/search/all/?term=1960972624>, printed on May 20, 2019.*
Hirschhorn et al. Genetics in Medicine. vol. 4, No. 2, pp. 45-61, Mar. 2002.*
Lucentini et al The Scientist (2004) vol. 18, p. 20.*
Langdahl et al Journal of Bone and Mineral Research (2000) 15: 402-414.*
Li et al BMC Genetics. 2010. 11:47.*
Gagneux et al. Molecular Phylogenetics and Evolution. 2001. 18: 2-13.*
Halushka et al. Nature. Jul. 1999. 22: 239-247.*
NCBI Database Gen Bank Accession No. NC 027301.1 (available at URL:<.ncbi.nlm.nih.gov/nuccore/NC_027301.1/, Sep. 22, 2015>).*
Baldán A, Tarr P, Lee R, and Edwards PA (2006) ATP-binding cassette transporter G1 and lipid homeostasis. Curr Opin Lipidol. 17:227-32.
Chang CC, Chow CC, Tellier LCAM, Vattikuti S, Purcell SM, and Lee JJ (2015) Second-generation PLINK: rising to the challenge of larger and richer datasets. Gigascience, 4:7.
Cingolani P, Platts A, Wang LL, Coon M, Nguyen T, Wang, Land SJ, Ruden DM, and Lu X (2012) A program for annotating and predicting the effects of single nucleotide polymorphisms, SnpEff: SNPs in the genome of *Drosophila melanogaster* strain w1118; iso-2; iso-3. Fly 6:2.
Davidson WS, Koop BF, Jones SJM, Iturra P, Vidal R. et al. (2010) Sequencing the genome of the Atlantic salmon (*Salmo salar*). Genome Biology 11: 403.
Ferrucci L, Perry JRB, Matteini A, Perola M, Tanaka T et al. (2009) Common variation in the beta-carotene 15, 15'-monooxygenase 1 gene affects circulating levels of carotenoids: A genome-wide association study. American Journal of Human Genetics 84: 123-133.
Garrison E and Marth G (2012) Haplotype-based variant detection from short-read sequencing. arXiv: 1207.3907v2 [q-bio.GN].
Hendrickson SJ, Hazra A, Chen C, Eliassen AH, Kraft P et al.(2012) β-Carotene 15,15'-monooxygenase 1 single nucleotide polymorphisms in relation to plasma carotenoid and retinol concentrations in women of European descent. American Journal of Clinical Nutrition 96:1379-1389.
Industry Standards for Fish (1999) Standard for quality grading of farmed salmon, Industry standard NBS 10-01; http://fhl.nsp01cp.nhosp.no/files/Quality_grading_of_farmed_salmon.pdf.
Jlali M, Graulet B, Chauveau-Duriot B, Chabault M, Godet E et al. (2012) A mutation in the promoter of the chicken β, β-carotene 15,15'-monooxygenase 1 gene alters xanthophyll metabolism through a selective effect on its mRNA abundance in the breast muscle. Journal of Animal Science 90:4280-4288.

(Continued)

*Primary Examiner* — Carla J Myers
(74) *Attorney, Agent, or Firm* — Shook, Hardy & Bacon L.L.P.

(57) ABSTRACT

The present invention relates to a method of predicting the ability of a salmonid to utilise dietary pigment, the method comprising determining the alleles present at one or more DNA polymorphism in the abcg 2 gene in the salmonid and predicting the ability of the salmonid to utilise dietary pigment based on the determination of the alleles. Such a method may be used in a method of selecting a salmonid for use as broodstock. The present invention also relates to a method of genome editing in order to create a salmonid with an increased ability to utilise dietary pigment, the method comprising editing the genome of the salmonid in order to introduce one or more red allele of a DNA polymorphism in the abcg2 gene.

6 Claims, 6 Drawing Sheets

Specification includes a Sequence Listing.

(56) References Cited

OTHER PUBLICATIONS

Le Bihan-Duval E, Nadaf J, Berri C, Pitel F, Graulet B et al. (2011) Detection of a cis eQTL controlling BCMO1 gene expression leads to the identification of a QTG for chicken breast meat color Plos One 6.

Li H and Durbin R (2009) Fast and accurate short read alignment with Burrows-Wheeler Transform. Bioinformatics 25: 1754-60.

Lietz G, Lange J, and Rimbach G (2010) Molecular and dietary regulation of beta,beta-carotene 15, 15'-monooxygenase 1 (BCMO1). Archives of Biochemistry and Biophysics 502:8-16.

Moen T, Baranski M, Sonesson AK, Kjøglum S (2009) Confirmation and fine-mapping of a major QTL for resistance to infectious pancreatic necrosis in Atlantic salmon (*Salmo salar*): population-level associations between markers and rail.

Pathak E, Mishra R (2013) Role of highly central residues of P-loop and its flanking region in preserving the archetypal conformation of Walker a motif of diverse P-loop NTPases. Bioinformation 9:23-28.

Pathak E, Mishra R (2014) Analysis of P-Loop and its Flanking Region Subsequence of Diverse NTPases Reveals Evolutionary Selected Residues. Bioinformation 23:216-220.

Telbisz Á, Özvegy-Laczka C, Hegedüs T, Varadi A, and Sarkadi B. (2013) Effects of the lipid environment, cholesterol and bile acids on the function of the purified and reconstituted human ABCG2 protein. Biochem J. 450:387-95.

Uimari P, Kontkanen O, Visscher PM, Pirskanen M, Fuentes R, and Salonen JT (2005) Genome-wide linkage disequilibrium from 100,000 SNPs in the East Finland Founder population. Twin Research and Human Genetics 8: 185-197.

International Search Report and Written Opinion dated in Appl. No. PCTGB2016/053963, 11 pages.

Hilde Sundvold et al: "Characterisation of a novel paralog of scavenger receptor class B member I (SCARB1) in Atlantic salmon (*Salmo salar*)", BMC Genetics, Biomed Central, GB, vol. 12, No. 1, May 30, 2011 (May 30, 2011), p. 52, XP021102217, ISSN: 1471-2156, DOI: 10.1186/1471-2156-12-52 abstract; p. 7, right-hand col., 2nd para.

Jorgen Odegard et al: "Genomic prediction in an admixed population of Atlantic salmon (*Salmo salar*)", Frontiers in Genetics, vol. 5, Nov. 21, 2014 (Nov. 21, 2014), XP055353022, DOI: 10.3389/fgene.2014.00402 the whole document.

Zaja R et al: "Cloning and mRNA expression analysis of an ABDG2 (BCRP) efflux transporter in rainbow trout (*Oncorhynchus mykiss*) liver and primary hepatocytes", Marine Environmental Research, Applied Science Publishers, Barking, GB, vol. 66, No. 1, Jul. 1, 2008 (Jul. 1, 2008), p. 77-79, XP022711677, ISSN:0141-1136, DOI: 10.1016/J.MARENVRES.2008.02.028, the whole document.

Sigbja RN Lien et al: "A dense SNP-based linkage map for Atlantic salmon (*Salmo salar*) reveals extended chromosome homeologies and striking differences in sex-specific recombination patterns", BMC Genomics, Biomed Central Ltd, London, UK, vol. 12, No. 1, Dec. 19, 2011 (Dec. 19, 2011), p. 615, XP021093244, ISSN: 1471-2164, DOI: 10.1186/1471-2164-12-615, the whole document.

\* cited by examiner

TEST FOR PREDICTING THE ABILITY OF A SALMONID TO UTILISE DIETARY PIGMENT

CROSS-REFERENCE TO RELATED APPLICATIONS

This application claims priority under 35 U.S.C. § 371 to PCT Application PCT/GB2016/053963, filed Dec. 16, 2016, which claims priority to GB patent application number 1522230.0, filed on Dec. 16, 2015, the entirety of the aforementioned applications is incorporated by reference herein.

SEQUENCE LISTING

A text file in compliance with ASCII and having a ".txt" extension has been electronically submitted via EFS-Web. The text file named "Sequence Listing" was created on Jun. 14, 2018 and is 15.4 KB. The text file is expressly incorporated by reference herein in its entirety.

The present invention relates to methods for predicting the ability of a salmonid to utilise dietary pigment, more specifically the invention relates to predicting the ability of a salmonid to utilise dietary pigment by the analysis of DNA polymorphisms.

Consumers of salmonid have a preference for fish that can be prepared as a fillet that is deep red in colour in its raw (eg un-cooked) and fresh state, as well as in processed products. The fillet of a salmonid (being a single side of the body of a fish, with the bones removed) is mostly composed of muscle tissue. It is the colour of this muscle tissue in the fillet that provides the deep red colour that is most prized by consumers. As a result, salmonids that provide a fillet that is deep red in colour are more easily sold and can be sold for a higher price than salmonid with fillets of a paler more pink colour. Salmonid producers are therefore incentivised to rear salmonid with the above-mentioned desired deep red fillet colour.

The red colour of the salmonid fillet is caused by dietary carotenoids, in particular astaxhanthin, and (to a lesser extent) canthaxanthin. The pigments responsible for the red colour in wild salmonid fish originate from their natural feeding on small crustaceans. The pigments are catabolised in the liver, forming metabolites that are excreted from the body. However, a fraction of the ingested pigment is deposited in muscle tissue rather than being catabolised. The pigments causing the red colour of salmonid tissue is not a natural part of the diets fed to farmed salmonid, so the carotenoids, most importantly astaxhanthin, is therefore added to the commercial feed so that the salmonid can obtain the red colour wanted by consumers. Salmonid farmers use this technique to ensure that the intensities of the red colour of the salmonid fillets are high enough to meet their customers' demands, as well as the quality standards of the industry. Norwegian Atlantic salmon farmers, for example, have agreed upon lower limits of the red colour intensity (Industry Standards for Fish, 1999); batches of salmon having a red fillet colour intensity below this lower limit are deemed to be unfit for the consumer market.

The addition of pigments to a salmonid's diet adds a significant cost to the production of the salmonid; the cost of providing the pigment for the life of an average fish (weighing about 5.5 kg at slaughter) is estimated to represent 2-3% of the total production cost per kg of fish. Reducing the amount of pigment required, whilst still being able to rear salmonids with the desired fillet colour, would have a significant impact on the profits of salmonid farming. Hence, the salmonid producers are interested in rearing salmonids that are inherently efficient at retaining the dietary pigments. The salmonid producers are also interested in rearing salmonids that are inherently (i.e. genetically) similar in their ability to retain the dietary pigments, in order to ensure that all their salmonids have a high enough red fillet colour intensity, while at the same time avoiding the unnecessary expenditure relating to pigments on those animals that would in any case easily meet the fillet colour intensity threshold.

One approach towards increasing the redness of the salmonid fillets and/or reducing amount of pigment added to the feed is to select salmonids as broodstock on the basis of their fillet colour, thereby enabling the development of a population of salmonids that present the desired fillet colour even when the diet contains relatively small doses of astaxanthin. The redness of the salmonid fillet is determined by many factors, such as the amount of astaxanthin in the feed and the age/body size of the fish. However, genetic disposition is a major determinant of the fillet colour, typically responsible for around 40% of the total variation found in muscle pigment content or red colour intensity. Genetic selection for increased redness can therefore make it possible for producers to obtain, on average, significantly higher red colour intensities and/or a significant decrease in the amount of feed pigment required to reach a certain intensity. Genetic selection will also lead to a reduced variation, within the salmonid stock in question, in the ability to obtain the required red colour intensities.

In order to establish fillet colour, the skilled person can measure pigment concentration in the muscle of the salmonid by high-pressure liquid-chromatography (HPLC). However, such a method is time-consuming and costly, and requires the sacrifice of the animal. The fillet colour can be evaluated (1) by visual (ie by eye) comparison against the Roche SalmoFan®, (2) by automated inspection of digital photographs, or (3) by using automated systems for objective estimation of pigment concentration based on spectroscopy. Experimental measurements obtained using any of the three last-mentioned methods may be translated to units of pigment content (mg pigment per kg fillet) by correlating, in a sample of at least 50 animals, the measurements in question with HPLC-obtained pigment-content. As a rule of thumb, when farming Atlantic salmon, producers generally aim for an average pigment concentration of above 7 mg per kg fillet, corresponding to Roche SalmoFan® measurements at around 26 .

The drawback of the above-mentioned methods for estimating the intensity of the red colour in salmonid fillets is that they all require that the salmonid first be slaughtered and the fillet prepared. This not only reduces the number of salmonids that can be used to form the population of the broodstock, but also means that it is the siblings of the salmonids that have been analysed that are used as broodstock. The accuracy of selection is reduced when selection is performed on the basis of phenotypes that are not recorded on the selection candidates, meaning that the population of salmonid created from the broodstock may not possess the desired fillet colour that was presented by the tested animals.

There is therefore a need for alternative methodologies for predicting the ability of a salmonid to utilise dietary pigment, thereby enabling the selection of salmonids that have a greater than normal ability to utilise dietary pigment, and also the deselection of salmonids that have a lesser than normal ability to utilise dietary pigment.

The inventors of the present application have, following extensive experimentation, identified that one can predict a salmonid's ability to utilise dietary pigment by analysis of one or more DNA polymorphism. Predicting such an ability on the basis of DNA polymorphisms means that analysis can be carried out on a small tissue sample of the salmonid and that one does not need to sacrifice the salmon being analysed. Consequently, one can develop a population of salmonid directly from broodstock that have been analysed by the new DNA based method (ie marker-assisted selection). Surprisingly, the DNA polymorphisms have been found in the abcg2 gene in the salmonid. This gene encodes the ATP-binding cassette sub-family G member 2 protein. This protein is a transmembrane transporter that uses energy from ATP binding and hydrolysis to transport various substrates across the cell membrane. For example, the transporter protein has been demonstrated to transport lipids, diverse drug substrates, cholesterol and other steroids into the cell. The protein has been implicated in mechanisms for multi-drug resistance, protecting the foetus from xenobiotics in the maternal circulation and inhibiting cancer. There has been no link made between the ATP-binding cassette sub-family G member 2 proteins and the ability for a salmonid, or indeed any animal, to utilise dietary pigment.

Salmonids belonging to a population selected by this method will have a stronger red colour than salmon belonging to a population of salmon not selected by this method, given that the two populations are otherwise similar, and irrespective of the level of pigment in the feed. Thus, salmon belonging to a population selected by methods of the present invention will require less dietary pigment in order to reach a desired level of pigment.

Accordingly, in a first aspect of the present invention, there is provided a method of predicting the ability of a salmonid to utilise dietary pigment, the method comprising determining the alleles present at one or more DNA polymorphism in the abcg2 gene in the salmonid and predicting the ability of the salmonid to utilise dietary pigment based on the determination of the alleles.

The utilisation of pigment by a salmonid is the process of depositing and retaining the dietary pigment in the muscle tissue rather than catabolising and excreting it. The greater the percentage of total dietary pigment that can be extracted from the total dietary pigment and retained in muscle tissue, the greater the ability the salmonid has at utilising pigment (and vice versa). The greater the utilisation of pigment the more intense red colour will be presented by the salmonid fillet when compared to a fillet produced by a similar salmonid (e.g. weight and/or age) with a poorer level of utilisation of pigment and when both fish are fed the same level of dietary pigment Apart from practising the present invention, the relative level of utilisation of pigment of a test salmonid may be confirmed by analysis of the colour of the fillet (for example, by using any of the methods described above) and/or the amount of pigment in a fillet (optionally expressed as mg of pigment per kg of fillet), and comparing that level to that derived from a population of salmonid that are fed on a diet that includes the same or substantially the same amount of pigment as that of the test salmonid.

Salmonids that have a greater than normal ability to utilise dietary pigment are ideal broodstock as they will be able to maximise on the use of pigment in their diet in order to present the desired intense red colour for their fillets. Salmonids with a lesser than normal ability to utilise dietary pigment would not ideally be selected as broodstock.

Consequently, the method of the present invention may predict a salmonid that has a greater or a lesser than normal ability to utilise dietary pigment based on the determination of the alleles present at one or more DNA polymorphism in the salmonid.

For the avoidance of doubt, a salmonid that has a greater (or lesser) than normal ability to utilise dietary pigment is most likely to have a muscle pigment content (and hence, a red colour intensity) which is higher (or lower, respectively) than the average muscle pigment content of the population that the salmonid belongs to.

The skilled person would be well aware of what such a normal population would be. However, for the avoidance of doubt, the population of salmonid may be defined as a contemporary group of salmonids, having been raised on the same feed and in the same environments (eg. in the same tanks and in the same net pens) throughout their lives. The population may be raised on commercially available, astaxhantin-containing, feed intended for, for example, farmed Atlantic salmon.

In practice, salmonids are usually or always farmed in large sea cages or water tanks, containing thousands of individuals (cohorts) of the same genetic origin and the same age, being fed the same feed ad libitum. Therefore, an individual animal should, and can easily be, compared with a random sample of its cohorts (for example, the random sample comprising at least 50 individuals), in order to determine whether its fillet colour is higher or lower than normal. Thus, an individual that has been selected (using the methods described here) to have a higher than normal ability to utilise pigment (eg astaxhantin) is expected to have a concentration of pigment which is higher than the mean pigment concentration within a random sample of its cohorts.

The presence or absence of the appropriate alleles of the DNA polymorphisms of the present invention can define whether the salmon has a greater or lesser than normal ability to utilise dietary pigment.

It should be noted that the method of predicting a salmonid with a greater or lesser ability than normal to utilise dietary pigment, based on the determination of the alleles present at a DNA polymorphism, only applies if the DNA polymorphism in question is variable within the salmonid population in question (ie if more than one allele of the DNA polymorphism is present within the population). One may determine whether or not a DNA polymorphism is variable within a population by genotyping at least 50 random animals from the population for the DNA polymorphism in question; the population may be defined to be variable if at least one copy of the rare allele (ie whichever of the alleles available is in the lowest number at the DNA polymorphism) is found within these 50 random animals.

The skilled person would be well aware of the target colour for consumers, but for the avoidance of doubt, Atlantic salmon fillets that possess the desired high intensity red colour may have a pigment content of at least 7 mg per kg of fillet and/or the equivalent of a Roche SalmoFan® score of 28 or more. Assuming the salmon are fed a normal dietary level of pigment (for example, 40-50 mg astaxhantin per kg of feed), salmon identified by the present invention to have a greater than normal ability to utilise pigment would likely present a pigment content of 7 mg per kg of fillet or more and/or the equivalent of a Roche SalmoFan® score of 28 or more. Salmon identified by the present invention to have a lesser than normal ability to utilise pigment would likely present a pigment content of less than 7 mg per kg of fillet and/or the equivalent of a Roche SalmoFan® score of less than 28.

The inventors have found that the DNA polymorphisms of the present invention can be present in either of two forms, i.e. the polymorphisms each have two alleles. One allele can be characterised as being associated with a salmonid that has a greater than normal ability to utilise dietary pigment. Salmonids that are homozygous for this allele would be expected to present fillets with a higher red colour intensity than normal (assuming the diet of that population includes pigment). Consequently, this allele is referred to hereinafter as the "red allele". The other allele can be characterised as being associated with salmonids having less than normal abilities to utilise dietary pigment. Salmonids that are homozygous for the other allele would be expected to present fillets with a lower red colour intensity than normal (assuming the diet of that population includes pigment). Consequently, this allele is referred to hereinafter as the "pale allele". A normal ability to utilise dietary pigment is defined as the mean ability (to utilise pigment) of the salmonid population in question. It is customary (part of the Art) and reasonable to assume that the ability to utilise dietary pigment correlates strongly with the pigment (e.g. astaxhantin) levels found in the muscle of individuals that have ingested pigment through the feed. Thus, estimates of pigment levels in muscle can be used as measures of the ability to utilise dietary pigment, and a normal ability to utilise dietary pigment translates to a normal pigment content in muscle. In any given population (subject to one and the same environment), the normal pigment level would be defined as the mean pigment level in a number of (for example, at least 50) random animals from the population.

Normal salmonids are diploid organisms, and so possess two copies of the polymorphisms of the present invention (one copy to be found in each set of chromosomes). The step of determining the alleles in the method of the first aspect of the present invention therefore includes the step of analysing the form of DNA polymorphism provided in each set of chromosomes, i.e. determining whether each copy of the DNA polymorphism present is a red allele or is a pale allele. When a salmonid subjected to the method of the present invention is determined to have two copies of the red allele for the DNA polymorphism (i.e. the salmonid is homozygous for the red allele), the salmonid is predicted to have a greater than normal ability to utilise pigment. Consequently, assuming such salmon are provided with pigment enriched diets, those fish would be expected to achieve a more intense red coloured fillet than normal fish fed on the same diet. Conversely, when a salmonid subjected to the method of the present invention is determined to have two copies of the pale allele for the DNA polymorphism (i.e. is homozygous for the pale allele), the salmonid is predicted to have a lesser than normal ability to utilise pigment. Consequently, assuming such salmonids are provided with pigment enriched diets, those fish would be expected to achieve a lower intensity of red coloured fillet than normal fish fed on the same diet. When a salmonid subjected to the method of the present invention is determined to have one copy of the red allele for the nucleotide polymorphism and one copy of the pale allele for that nucleotide polymorphism (i.e. is heterozygous), the salmonid would be predicted according to the present invention to have a greater than normal ability to utilise pigment, if the red allele is less frequent in the population than the pale allele (possibly only a slightly greater ability). Consequently, assuming such salmonids are provided with pigment enriched diets, those fish would be expected to achieve a more intense red coloured fillet than a population of normal fish fed on the same diet. Conversely, if the red allele is slightly more frequent in the population than the pale allele, a heterozygous animal would be predicted to have a lesser than normal ability to utilise pigment (possibly only slightly lower), and so would be expected to have a lower red colour intensity when compared to the average of the normal population of fish fed on the same diet Some salmonids may be triploid, i.e. have three copies of each chromosome. For example, some salmon in aquaculture have been rendered triploid through heat- or pressure shocks; these individuals have inherited both chromosome sets from their mothers, but only one set from their fathers. Triploid animals may have three copies of the red allele. These animals will be predicted to have a greater than normal ability to utilise pigment. Triploid animals may have three copies of the pale allele. These animals will be predicted to have a lesser than normal ability to utilise pigment. A triploid animal may have two copies of the red allele and one copy of the pale allele, or it may have one copy of the red allele and two copies of the pale allele. For these animals, and for all animals, the rule applies that an animal is expected to have a greater ability to utilise dietary pigment the more copies of the red allele it has.

The skilled person would be well aware of the gene abcg2 in salmonids.

For the avoidance of doubt, for example, in Atlantic salmon, the gene is the gene having identifier LOC106595425 within the Gene partition of the database hosted by the National Center for Biotechnology Information (NCBI, USA; http://www.ncbi.nlm.nih.gov/). Within the Atlantic salmon genome, LOC106595425 is located within the region stretching from position 71,393,258 to 71,417,739 of the DNA sequence of Atlantic salmon chromosome 2 (GenBank identifier NC_027301.1). Fine mapping of the chromosome sequence harbouring LOC106595425 has shown that there are actually two abcg2 genes in this region. The two copies of abcg2 are interspersed by a gap in the genome sequence, i.e. a part of the genome sequence within the region is missing. One of the two copies is of particular interest in the current context, this copy will be referred to as abcg2 hereinafter. Using RNAseq data from 10 AquaGen salmon, the complete coding (transcribed) sequence of abcg2, including the protein-coding region, has been characterized. SEQ ID NO:1 corresponds to the DNA sequence of the coding (i.e. transcribed) part of abcg2, whereas SEQ ID NO:2 and SEQ ID NO:3 are the protein sequence corresponding to that transcript (SEQ ID NO:2 is the amino acid sequence of Abcg2 derived from a genome including a red allele, whilst SEQ ID NO:3 is the amino acid sequence of Abcg2 derived from a genome including the pale allele). R=A or G in SEQ ID NO: 1. The protein product of the abcg2 gene will be referred to as Abcg2 (capital first letter, no italics).

SEQ ID NO: 1:-
5'TCTCTCTCTCTCCTTCTCCCTCTTTCTGTGAGGAGGATGTCTAAGCCCC

AGAATGGTGAGCCAGGCAGCCCAGCAGGAGTCCCAGCAGCAGATGATCCA

GAGGTGATGTTCCAGGTGCCTGGTCCAACCGTCTCCTTCTCCAGACTACA

CTACTCTGTCATGGAGAGCAATGGACTCTGCCACAAGAGAGAAACTGAGA

AACACATCCTCAAAGACGTTAGCGGCATCATGAGACCAGGGATGAACGCC

ATCATGGGGCCAACAGGAAGTGGAAAAACATCTCTCCTGGATGTGATAGC

AGGTCGTAAGGACCCAGCAGGGTTGAAGTTTGGTCAGGTTCTGGTCGATG

GGAAGATGGTGGACTCTGACCTCCGACTCATATCTGCCTACGTGGTGCAG

```
GATGATATATTGATGGGAACCCTGTCAGTGAGAGAGAACTTGTTGTTCAG

TGTGAACCTGAGACTAGACCCTAGACATTATTGTACAGCTGACAAACAGC

AGAGAGTAGACAGCATCATAGAAGACCTGGGACTACAGGACTGTGCCCAC

ACCAAGATAGGAACAGAGTTCCTGCGTGGTGTGTCTGGGGGAGAGAGGAA

GAGGTGCAGCATCGGTATGGAGCTGATTACTTCTCCTTCTCTTCTGTTCC

TGGATGAACCCACCACTGGTCTGGACTCTAACACTGCTAACCATATCATC

AAGCTGCTGCATAGGCTGTCTAGAARCGGTAAGACTATCGTCTTCTCCAT

CCATCAGCCTCGTTACTCAATCTTCAGCCGCTTTGACCACCTGACCCTGA

TGCACCGAGGAGAGTTGGTGTATGCTGGAGCTGCCGGGAAGGCCCTGAGC

TACTTCACTGACCTGGGGTATCACTGTGAGCCGTTCAACAACCCATCTGA

CTTCTTCCTAGACATCACTAACGGAGAGGCTCAGTCTACACTGGACATCA

CTTCATTTAACTATGAGGAACTGTGACAACAGCAACCTTCTGGCAGTG

AGCTACAGACAGTCGGCTCAGTACCAGAGGGTGGTGGAGGAGCTGGACCA

TTTGACCCAGGGTCTGGAGGGAGGGGTTGGAGGTCAGGGACAGAAGGCCG

ACTACGTCACCTCCTTCTGGTACCAGATAAGGATAGTGTGTGGTCGTACG

GTGATGAACTCTCTCAGGAACCCCCAGACATCGTACGCTCAGCTTGCCCT

TAACATCTTCTTCGCTCTGCTGGTCGGCCTCATCTACTACCAGATCCCCC

TGACTCTACCTGAAGCCCTACAGAACAGGATGGGAGCATTCTTTTTCCTC

ATCATCAACATGGTGTTTGGGAATCTTTCAGCTGTGGAACTCTTCATCAA

TGAGAGAGCTCTGTTCATCCATGAGAACTCTAGTGGGTACTACCGTACGT

CCGTCTACTTCCTGTCTAAGATATTCGCTGACCTCATCCCCAACCGCATT

GTACCTATCTTCATCTTCTCAGCCATCGCCTACTATATGATGGGTCTGAA

GCCAGCCGTCACAGCGTTCCTGCTCTTTGCGCTGACGATGTCCCTGGTCA

GTCTAGCTGGGGTCAGTCTAGCGTTCCTGGTATCAGCCTCTGTCTCCTCC

TTCGCTATGGCCAACGTCCTCATCGCGCTGCCTTTCGTCTTCATGATGGT

GTTTGGAGGGTTCCTGGTCAACCTTAACTCCATGTTGTCCTGGCTGTCAT

GGCTGAAATGGATCAGCATCTTCCGCTACGGCCTAGAGGCTGTGACCATC

AATGAGTTTAAAGGACAGATATTCTACAGCAACACAACCATTCTTCCAGG

GGAGGTGTACCTGGAGACCCAGGGAATAGACTACAGCACCTGGGGTTTCT

GGCAGAACCATGTAGCTCTGGGTGGGATCATTACGGTGTGTATGGTCTTG

GCCTACATACAGCTCAGACGGATCAACCGCTGGAAGTAACACATGAAACT

ACACCTTCTGGAACAACAGGGACTGTGAAGAGACACACACCACAGGCACA

CACGCACGCAAGCACACGCACTCTCCACTCTAGTACATTGTAATATTGTT

GTATGGTTGTATTGTACATTTTGTGTTGTAGAAATGTAGTGGTGTAATAA

TGTTATATGATGTGCTGTTGATCTTGTTTTTTGGTGCCTTAATACAGTCT

AAGTCCTGTCTATGCCGGGGAGGGGTTCTACTGAACTATATGGAATTGT

TTTAACAAGGTCATACCAAGGATCTTTTTGTTATTTGATTTAGAATTTTA

AGACTCCTTGAGGCAATATATAAAACAAATATTTGATGAACATTTTTATT

TGGCCTTACTGCTGTTAACCCATAGAAACACATTGAATAACAGATTCACT

ACGTGGAACAACAGACAGTCCCAGAACAAAATGTAAAGGAAGTCTGATGT

GTCTGTCCTATATCTGAGAGATAAAAGAAACATATGGAAAAAAAAA3'

SEQ ID NO: 2:-
MSKPQNGEPGSPAGVPAADDPEVMFQVPGPTVSFSRLHYSVMESNGLCHK

RETEKHILKDVSGIMRPGMNAIMGPTGSGKTSLLDVIAGRKDPAGLKFGQ

VLVDGKMVDSDLRLISAYVVQDDILMGTLSVRENLLFSVNLRLDPRHYCT

ADKQQRVDSIIEDLGLQDCAHTKIGTEFLRGVSGGERKRCSIGMELITSP

SLLFLDEPTTGLDSNTANHIIKLLHRLSRNGKTIVFSIHQPRYSIFSRFD

HLTLMHRGELVYAGAAGKALSYFTDLGYHCEPFNNPSDFFLDITNGEAQS

TLDITSFNYEENCDNSNLLAVSYRQSAQYQRVVEELDHLTQGLEGGVGGQ

GQKADYVTSFWYQIRIVCGRTVMNSLRNPQTSYAQLALNIFFALLVGLIY

YQIPLTLPEALQNRMGAFFFLIINMVFGNLSAVELFINERALFIHENSSG

YYRTSVYFLSKIFADLIPNRIVPIFIFSAIAYYMMGLKPAVTAFLLFALT

MSLVSLAGVSLAFLVSASVSSFAMANVLIALPFVFMMVFGGFLVNLNSML

SWLSWLKWISIFRYGLEAVTINEFKGQIFYSNTTILPGEVYLETQGIDYS

TWGFWQNHVALGGIITVCMVLAYIQLRRINRWK

SEQ ID NO: 3:-
MSKPQNGEPGSPAGVPAADDPEVMFQVPGPTVSFSRLHYSVMESNGLCHK

RETEKHILKDVSGIMRPGMNAIMGPTGSGKTSLLDVIAGRKDPAGLKFGQ

VLVDGKMVDSDLRLISAYVVQDDILMGTLSVRENLLFSVNLRLDPRHYCT

ADKQQRVDSIIEDLGLQDCAHTKIGTEFLRGVSGGERKRCSIGMELITSP

SLLFLDEPTTGLDSNTANHIIKLLHRLSRSGKTIVFSIHQPRYSIFSRFD

HLTLMHRGELVYAGAAGKALSYFTDLGYHCEPFNNPSDFFLDITNGEAQS

TLDITSFNYEENCDNSNLLAVSYRQSAQYQRVVEELDHLTQGLEGGVGGQ

GQKADYVTSFWYQIRIVCGRTVMNSLRNPQTSYAQLALNIFFALLVGLIY

YQIPLTLPEALQNRMGAFFFLIINMVFGNLSAVELFINERALFIHENSSG

YYRTSVYFLSKIFADLIPNRIVPIFIFSAIAYYMMGLKPAVTAFLLFALT

MSLVSLAGVSLAFLVSASVSSFAMANVLIALPFVFMMVFGGFLVNLNSML

SWLSWLKWISIFRYGLEAVTINEFKGQIFYSNTTILPGEVYLETQGIDYS

TWGFWQNHVALGGIITVCMVLAYIQLRRINRWK
```

Consequently, when the salmonid is an Atlantic salmon, the abcg2 gene may be that defined by SEQ ID NO: 1.

It is well within the ordinary skill to identify corresponding gene locations for the abcg2 gene in other salmonids, based on the above information. This is particularly simple as this region of the salmonid genome is relatively well conserved amongst salmonids. Nevertheless, the following is provided by way of further guidance.

In rainbow trout, the abcg2 gene may be the gene encoding the mRNA sequence which has GenBank identifier NM_001124683.1 or GenBank identifier EU163724.1, but it may also be the gene encoding a paralogue of that gene. Paralogues are genes within the same species derived from the same ancestral gene. Paralogues of a gene will have higher sequence similarity to each other than they will have to any other gene from the same genome.

In coho salmon, and in other salmonids apart from those mentioned, the mRNA of an abcg2 gene will have higher sequence similarity to the abcg2 gene from rainbow trout (NM_001124683.1) or paralogues of that gene, than to any other gene within the rainbow trout genome.

The above definition of an abcg2 gene is limited to the transcribed region of a gene, i.e. the part of the gene which gives rise to an mRNA molecule during transcription. However, the upstream and downstream regions of a gene, such as abcg2, may contain DNA polymorphism that influence the level of transcription of the gene, and hence, the effect of the gene on a phenotype. Such elements are commonly referred to as cis-acting DNA polymorphisms; they are frequently binding sites for proteins that modify the level of transcription of a nearby gene (such as in this case, abcg2). For example, a DNA polymorphism may be located 100 base pairs upstream of the first exon of the abcg2 gene, and be the binding site for a protein (a transcription factor) that regulates the transcription of abcg2. If one allele of the DNA polymorphism allows for better binding of the transcription factor than the other allele does, then the two alleles of the DNA polymorphisms will be associated with different transcription levels of the abcg2 gene, and hence, with different abilities to utilise dietary pigment. Accordingly, reference to the abcg2 gene in the methods of the present invention may be interpreted more broadly so as to encompass a gene region, the abcg2 region would encompass the upstream and downstream regions of the abcg2 gene. In particular, the abcg2 region would encompass the promoter region of the abcg2 gene; the region to which the transcription machinery and their associated transcription factors bind. The promoter region of the abcg2 gene would encompass the region stretching from 1 kb upstream of the first exon of the abcg2 gene, to the end of the gene, i.e. from position 71,393,258 to position 71,418,739 of the DNA sequence of Atlantic salmon chromosome 2 (GenBank identifier NC_027301.1).

The salmonid could be an Atlantic salmon. However the salmonid could be any salmonid, ie any other species which is a member of Salmoninae subfamily of the Salmonidae family within the order of Salminoformes. For example, the salmonid can be a salmon, charr or a trout. When the salmonid is a trout, it could be a brown trout (Salmo trutta) or rainbow trout (Oncorhynchus mykiss). When the salmonid is a salmon, it could be a coho salmon (Oncorhynchus kisutch), pink salmon (Oncorhynchus gorbuscha) or Atlantic salmon (Salmo salar). When the salmonid is a charr it could be an Arctic Charr (Salvelinus alpinus). The salmonid could be Atlantic salmon, coho salmon or rainbow trout The DNA polymorphisms of the present invention are therefore to be found within or close to the abcg2 gene. This means that the DNA polymorphisms of the present Invention are located within an exon of the abcg2 gene, or in between two exons of the abcg2 gene, or 100 base pairs or less distant from an exon of the abcg2 gene.

The DNA polymorphisms of the present Invention may influence the activity of the abcg2 gene.

The DNA polymorphisms of the present Invention have the ability to predict the ability of a salmon to utilise dietary pigment.

The DNA polymorphism may be NC_ 027301.1_ 71404326 (herein referred to as SNP No. 1).

Also, methods of the invention may employ SNP No. 1 in combination with any one or more additional polymorphisms.

SNP No. 1, as an example, in Atlantic salmon, is located within the protein-coding region of a gene, ATP-binding cassette transporter sub-family G member 2b (the protein will hereafter be referred to as Abcg2, the gene will be referred to as abcg2). The inventors have determined that SNP No. 1 is a causative polymorphism with regard to the ability to utilise dietary pigment, i.e. the two alleles (a red allele and a pale allele) that can be found at SNP No. 1 give rise to two different forms of the Abcg2 protein, one corresponding to a greater than normal ability to utilise dietary pigment, the other corresponding to a lesser than normal ability to utilise dietary pigment Therefore, DNA polymorphism No. 1 can be used in order to determine a salmon's ability to utilise dietary pigment.

A DNA polymorphism of the present Invention may be another DNA polymorphism causing an amino acid shift in the Abcg2 protein. The DNA polymorphisms may also be a DNA polymorphism which causes differences (between animals) in the concentrations of abcg2 mRNA or Abcg2 protein (regulatory DNA polymorphisms).

A DNA polymorphism of the present Invention may also be any DNA polymorphism being in moderate to strong linkage disequilibrium (LD) with SNP No. 1. Here a DNA polymorphism in moderate to strong LD with SNP No 1. is defined as any DNA polymorphism whose alleles are correlated with alleles at DNA polymorphism No. 1 with a squared correlation coefficient larger than 0.3. The squared correlation coefficient between alleles at two loci ($r^2$) is a commonly used measure of the level of LD between the two loci, and $r^2=0.3$ is a commonly used lower threshold for 'useful LD', the minimal LD needed in order for one locus being useable as an indicator of another locus (see e.g. Uimari et al. 2005).

The identity of that base which defines the red or pale allele for NC_027301.1 _71404326 for use in the methods of the present invention is provided in Table 2. For the avoidance of doubt, the red allele has the nucleobase thymine (T) at the variable position, whereas the pale allele has the nucleobase cytosine (C) at the variable position. The variable position is the position in the Atlantic salmon genome which corresponds to position 71,404,326 within GenBank sequence NC_027301.1.

The identity of the red- and pale alleles provided in Table 2 are relative to the DNA sequence provided in Table 3 (note: a DNA strand can be read in two directions, for example, the DNA sequence ACAGT would become ACTGT if read in the other (so-called reverse-complement) direction, and the middle base would be nominated as A or T, respectively, in these two cases). For example, when the methods of the present invention include the determination of the allele present at SNP No. 1, if the allele is determined to be T at the variant position of SNP No. 1 (defined by square bracket in Table 3), and provided that the DNA strand is read in the read direction used in Table 3, then the allele is determined to be a red allele. If the allele is determined to be C at the variant position of SNP No. 1 (provided that the DNA strand is read in the read direction used in Table 3), then the allele is determined to be the pale allele.

The associated sequence listing provides a sequence for each allele for each of the above described polymorphisms. SEQ ID NO:3 corresponds to the red allele for SNP No. 1. SEQ ID NO:4 corresponds to the pale alleles for SNP No. 1. For example, when a salmon is determined to have two copies of SEQ ID NO:3 at the DNA polymorphism corresponding to SNP No. 1 (i.e. two copies of the thymine (T) allele at that SNP), then that salmon is homozygous for the allele that confers a greater than normal ability to utilise dietary pigment. Consequently, that salmon is predicted, according to the present invention, to have a greater than normal ability to utilise dietary pigment. Conversely, when the salmon is determined to have two copies of SEQ ID NO:4 at the SNP corresponding to SNP No. 1 (i.e. two copies of the cytosine (C) allele at that SNP), then that salmon is homozygous for the allele that confers a lower than normal ability to utilise dietary pigment. Consequently, that salmon is predicted, according to the present invention, to have a lower than normal ability to utilise dietary pigment The identities of a polymorphism of the Invention can be found in Table 2. The dbSNP identifier is the identifier of the DNA polymorphism within the dbSNP database. By accessing the dbSNP database (www.ncbi.nlm.nih.gov), the sequence of the DNA polymorphism can be retrieved. The sequence are also to be found in Table 3. The "DNA polymorphism" identifier in Table 2 comprises the GenBank sequence wherein the DNA polymorphism resides (NC_027301.1), followed by underscore ("_"), followed by the position of the DNA polymorphism within the GenBank sequence. By accessing the GenBank database (www.ncbi.nlm.nih.gov), the GenBank sequence wherein the DNA polymorphism reside can be retrieved. By accessing the position of the DNA polymorphism within the GenBank sequence, the sequences flanking the DNA polymorphism can be extended, if needed.

The method may be applied to Atlantic salmon (i.e. Salmo salar). The method may be applied on another salmonid, i.e. another species which is a member of the Salmoninae subfamily of the Salmonidae family within the order Salmiformes. For example, the method may be applied on rainbow trout (Oncorhynchus mykiss) or on coho salmon (Oncorhynchus kisutch).

The step of determining which alleles are present in a salmon and at a specific DNA polymorphism may be practised on a sample taken from the salmon. The sample may be any sample in which analysis of nucleic acid material is possible, as would be readily understood by the person skilled in the art. For the avoidance of doubt, the sample may be a muscle tissue sample, blood sample, liver sample and/or a fin clip.

The skilled person would be well aware of all available methods capable of determining the genotypes (i.e. combination of alleles) that an animal has at a DNA polymorphism. For example, the method may involve sequence analysis of the salmon to be tested. Alternatively, the method may involve single base extension of DNA fragments terminating at the polymorphic site (e.g. iPLEX assays from Sequenom and Infinium assays from Illumina), allele-specific PCR (e.g. SNPtype assays from Fluidigm or KASPar assays from KBiosciences), or competitive hybridisation of probes complementary to the different alleles (e.g. the TaqMan assay from Applied Biosystems).

Consequently, in a further aspect of the present invention, there is provided a hybridisation probe that is specific for one or more of the aforementioned DNA nucleotide polymorphisms.

A salmon that is predicted to have greater than normal ability to utilise dietary pigment according to the first aspect of the present invention is more likely than normal to produce offspring that have greater than normal ability to utilise dietary pigment (and so ability to provide fillets with the desired high intensity red colour). Consequently, in a further aspect of the present inventions, there is provided a method of selecting a salmon for use as broodstock, wherein the salmon is selected based on the prediction by the method as claimed in the first aspect of the present invention that the salmon will provide a greater than normal ability to utilise dietary pigment.

Conversely, a salmon predicted by the method of the first aspect of the present invention as not providing a greater than normal utilisation of dietary pigment would not be selected as broodstock.

Also contemplated as forming part of the present invention is an isolated polynucleotide comprising one or more of the DNA polymorphisms selected from the group provided in Table 3, located within a portion of the salmon genome.

The realisation that DNA polymorphisms in the abcg2 gene are responsible for creating differences between individuals in the ability of a salmonid to utilise dietary pigment provides an understanding of the utility of genome editing in order to create a salmonid with an increased ability to utilise dietary pigment. For example, by using genome editing technologies, such as Zinc Finger Nucleases (ZFNs), Transcription Activator-Like Effector Nucleases (TALEN5), the CRISPR/Cas system, or engineered meganuclease re-engineered homing endonucleases, one may introduce the red allele at a SNP according to the present invention in individual salmonids and in populations of salmonids, thereby increasing the ability to utilise dietary pigment in individual animals and/or populations.

Consequently, in a further aspect of the present invention, there is provided a method of genome editing in order to create a salmonid with an increased ability to utilise dietary pigment, the method comprising editing the genome of the salmonid in order to introduce one or more red allele of a DNA polymorphism in the abcg2 gene. The DNA polymorphism could be SNP No. 1.

The present invention will now be described by way of example with reference to the accompanying figures, in which:

Figure 1A:
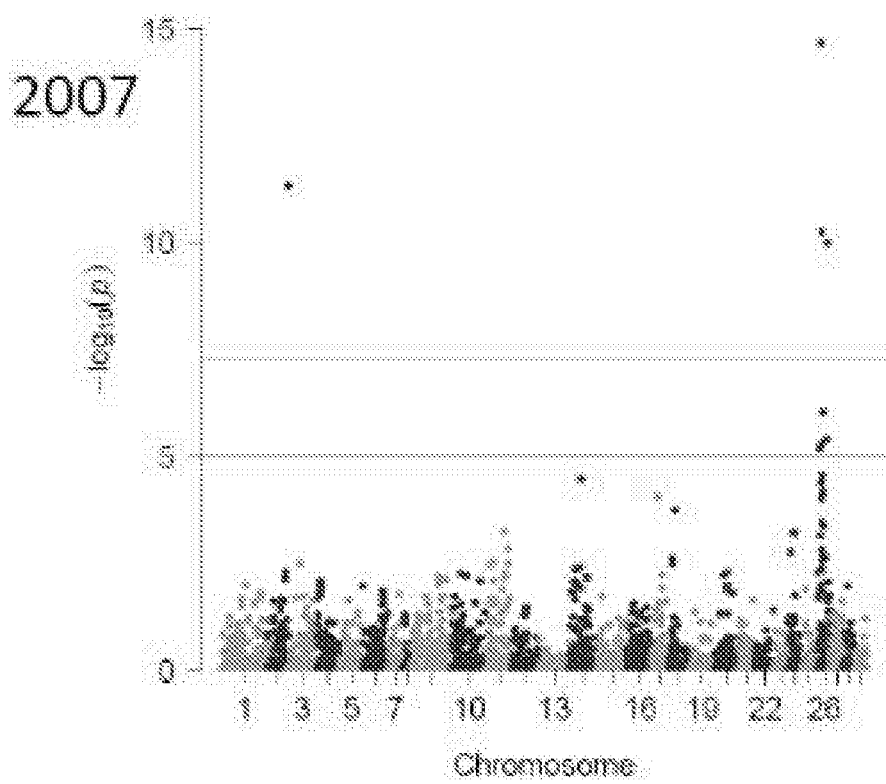
FIGS. 1a-1d displays Manhattan plots from GWAS experiments conducted on Sample sets 1 through 4, corresponding to experiments conducted in 2007, 2010, 2013, and 2014. Each dot of the plot corresponds to one SNP, the x-coordinate of the dot corresponding to the physical position of the SNP within the Atlantic salmon genome and the y-coordinate corresponding to the negative of the 10-based logarithm of the p-value of the test for association between fillet colour and genotypes at the SNP. The upper horizontal line corresponds to the threshold for experiment-wise significance (assuming H0 (null hypothesis; to be refuted) =none of the tested SNPs have an effect upon fillet colour, and H1 (alternative hypothesis): the SNP in question has an effect on fillet colour), and the lower horizontal line corresponds to a more lenient, "suggestive" level of significance.
Figure 1B:
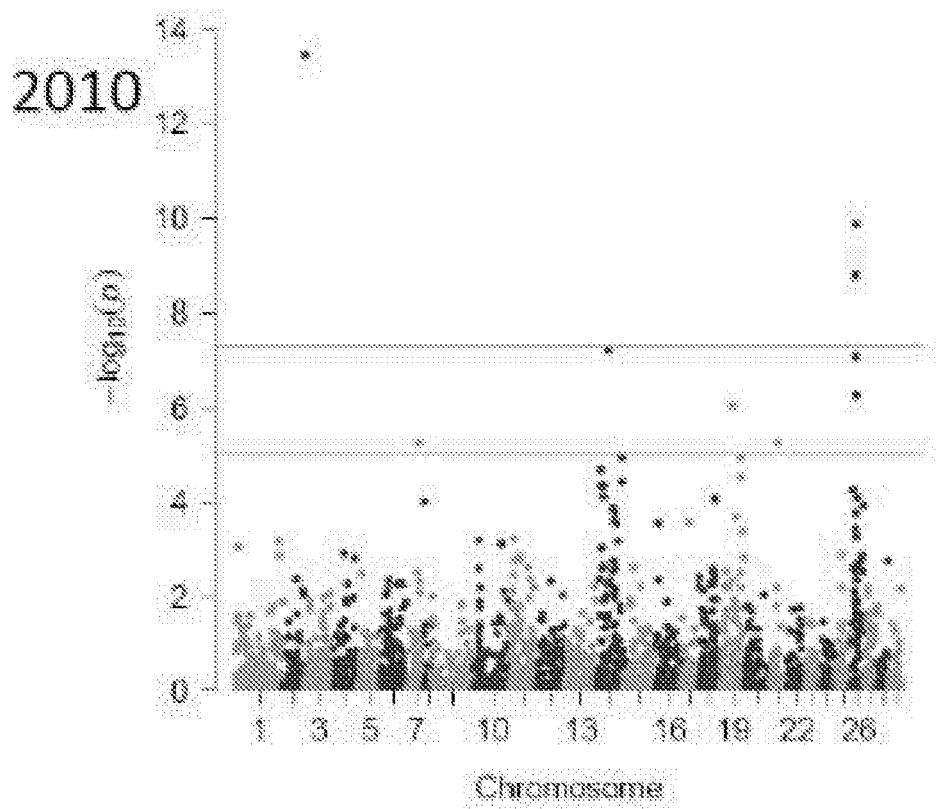
Figure 1C:
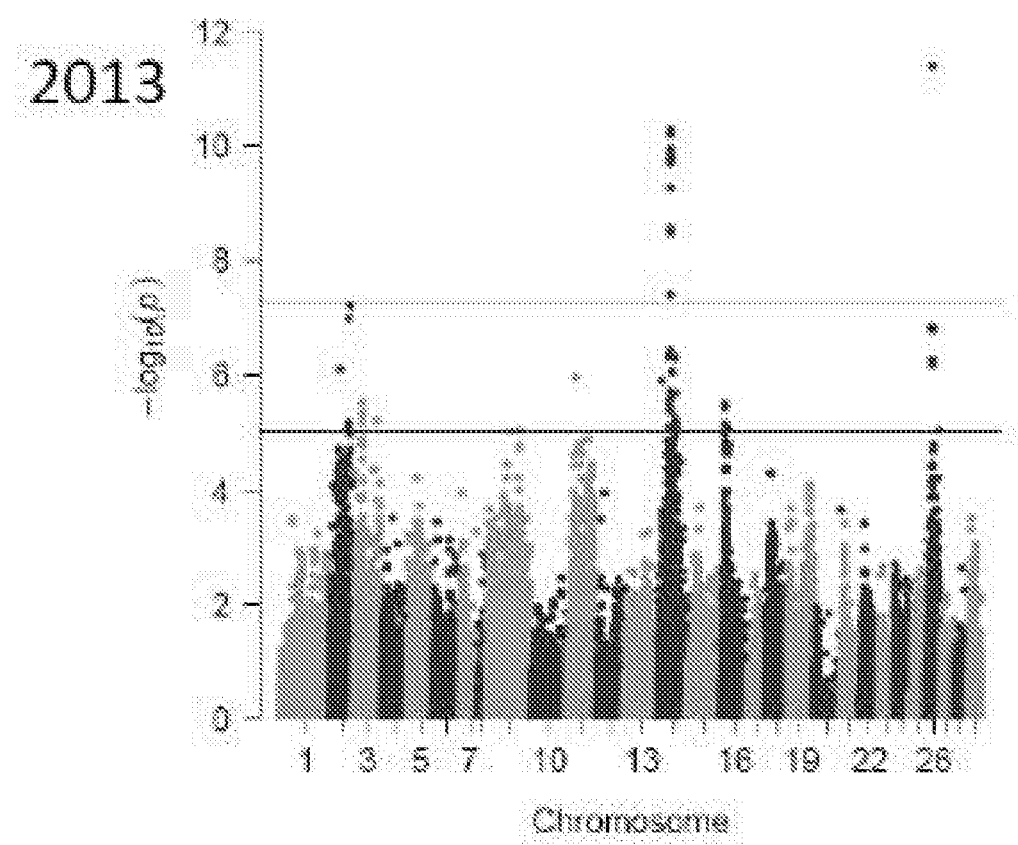
Figure 1D:
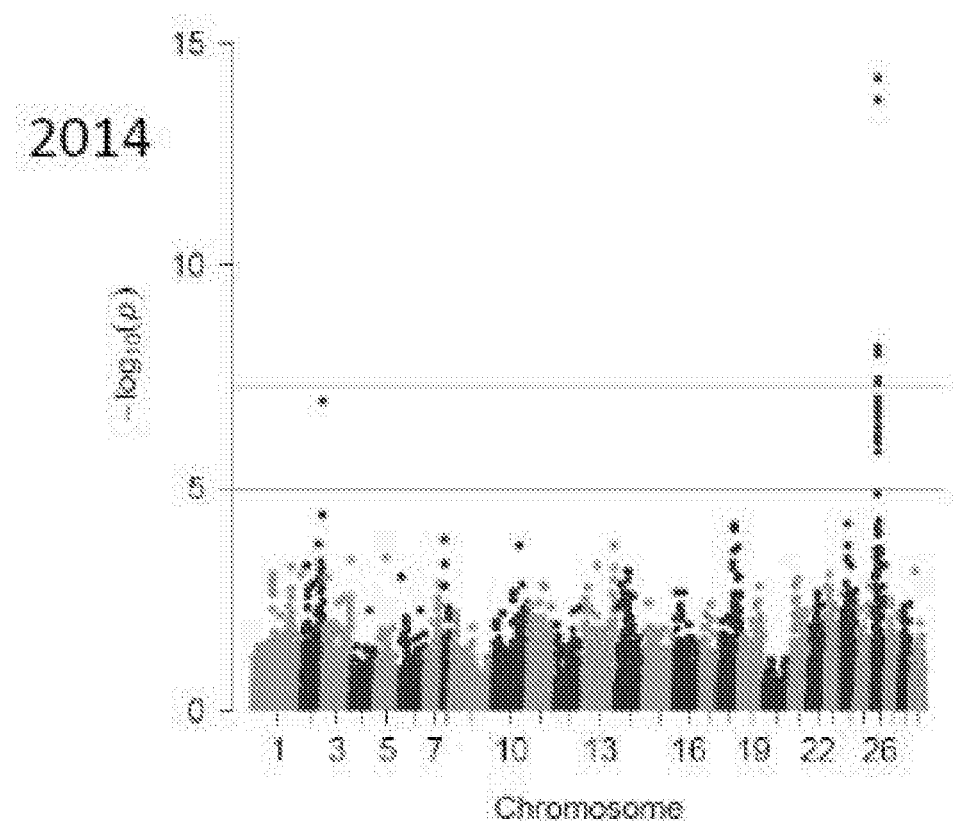

1. Fillet Colour Analysis of Test Animals

Fillet colour was analysed for salmon fillets taken from 6701 Atlantic salmon belonging to the AquaGen breeding population. This breeding population was formed in the early 1970s, on the basis of Atlantic salmon sampled from different Norwegian rivers.

Fillet colour was analysed in four independent test rounds, taking place in 2007, 2010, 2013, and 2014 respectively. In all four rounds, fillet colour was measured on the flesh side of fresh salmon fillets. In 2007 and in 2013, fillet colour was measured using a QVision Analyser, a spectrophotometer which measures absorption/reflection at 400-1200 nm wavelengths. In 2010, fillet colour was measured using the Photofish method, a method which is based on image analysis of photographs taken under standardised conditions (i.e. inside a closed box with constant light). In 2014, fillet colour was measured using Near-Infrared Spectroscopy (instrument: Foss XDS). Irrespective of method, the fillet colour measurements were converted to units of mg astaxhantin per kg of fillet. In each of the four test years, the conversions were based on the correlation between HPLC measurements and QVision/Photofish/Foss XDS Near Infrared measurements in a sample of 50 salmon that had been analysed by High-Performance Liquid Chromatography (HCPL) as well as by using QVision/Photofish/Foss XDS Near Infrared.

Within each of the four test rounds (2007, 2010, 2013, 2014), all fillet colour measurements were done under identical conditions.

In each test round, tissue samples (from skeletal muscle, liver, or heart) were taken from a subset of the animals whose fillet colour had been measured. DNA was extracted from these tissues using a standard method (using the DNAeasy 96 kit from QIAGEN, following the protocol supplied by QIAGEN). These DNA samples were later used for genotyping. In each test round, the selection of animals for DNA-extraction and genotyping was based on sets of criteria that were unrelated to the animals' fillet colour measurements or to the expected performance of the animal with regard to fillet colour.

From here on, the sample sets corresponding to the 2007, 2010, 2013, and 2014 test rounds will be referred to as Sample Set 1, Sample Set 2, Sample Set 3, and Sample Set 4. Sample Sets 1, 2, 3, and 4 were derived from consecutive generations of the AquaGen breeding nucleus. Table 1 displays the numbers of individuals, full-sib groups, fathers, and mothers pertaining to each sample set. Data sets 1, 2, 3, and 4 are the data sets corresponding to sample sets 1, 2, 3, and 4; the data sets encompassing genotype data and phenotype data.

containing approximately 6,000 working SNP-assays developed in-house at CIGENE. Of these 6,000 SNPs, 5650 were polymorphic within Sample Set 1. Sample Set 2 was genotyped using another custom-designed iSelect SNP-array from Illumina, this array being a slightly modified form of the array used on Sample Set 1. Of the approximately 6,000 working SNPs on this array, 4423 were polymorphic within Sample Set 2. The number of SNPs common to the two sets was 4308.

The SNP-arrays used for genotyping Sample Set 1 and Sample Set 2 contained SNPs that were mostly derived from the alignment of publicly available EST sequences or from sequencing of genome complexity reduction (GCI) libraries using 454 technology (Lien et al. 2011). The samples were genotyped following standard protocols for iSelect SNP-arrays, provided by Illumina. Bead-arrays were scanned on an iScan reader using a modified Infinium II scan settings protocol which records bead-level intensity data in .txt format.

Sample Set 3 was genotyped using a custom Axiom array from Affymetrix (San Diego, Calif., USA). The SNPs on this array were identified through whole genome sequencing of 29 Atlantic salmon from the AquaGen breeding nucleus in addition to three double haploid (androgenetically derived) Atlantic salmon. The SNP array contained 200,000 SNPs that were polymorphic within Sample Set 3. Genotyping was done according to the Axiom 2.0 Assay Manual Workflow User Guide (http://media.affymetrix.com/support/downloads/manuals/axiom_2_assay_manua l_workflow_prepguide.pdf). Genotype calling was done using the Affymetrix Power Tools programs (http://www.affymetrix.com/estore/partners_programs/programs/developer/tool s/powertools.affx), according to "best practices" recommendations from Affymetrix (http://media.affymetrix.com/support/downloads/manuals/axiom_best_practice_s upplement_user_guide.pdf).

Sample Set 4 was genotyped using a custom Axiom array from Affymetrix. The bulk of DNA polymorphisms on this array constituted a subset of the SNPs genotyped on Sample Set 3, but 3,719 were novel, i.e. not on the SNP chips used for genotyping Sample Sets 1-3. The technical details of genotyping of Sample Set 4 were identical to the technical details pertaining to Sample Set 3.

TABLE 1

Sample/data sets

| Data set | Year | Genotyping technol. | N animals | N FS groups | N fathers | N mothers | N markers | Mean weight (gram) |
| --- | --- | --- | --- | --- | --- | --- | --- | --- |
| 1 | 2007 | Illumina + Sequenom | 2891 | 265 | 177 | 141 | 5650 + 96* | 2845 |
| 2 | 2010 | Illumina 6k | 1847 | 308 | 241 | 242 | 4423 | 3024 |
| 3 | 2013 | Affymetrix 220k | 1963 | 99 | 68 | 69 | 219,998 | 3853 |
| 4 | 2014 | Affymetrix 56k | 1479 | 567 | 118 | 111 | 56,177 | 2636 |

Year = year of sampling and phenotypic measuring;
Genotyping technol. = technology used for genotyping the data set (see more detailed description below);
N animals = number of animals having been genotyped and phenotyped ('offspring');
N FS groups = number of full-sibling groups represented by genotyped and phenotyped animals;
N fathers and N mothers = number of fathers and mothers of the phenotyped and genotyped animals;
N markers = number of DNA polymorphisms genotyped.

*96 additional DNA polymorphisms were identified by de novo SNP-detection within a particular genomic region (the region containing the genes bcmo1 and bcmo1-like), these DNA polymorphisms were genotyped using Sequenom technology, whereas the other 5650 DNA polymorphisms were genotyped using Illumina technology.

2. Genotyping of Test Animals

Sample Set 1 was genotyped using a custom-designed iSelect SNP-array from Illumina (San Diego, Calif., USA), 3. Testing for association between SNP alleles and fillet colour In order to identify QTL for fillet colour, data sets 1, 2, 3, and 4 were analysed with a linear mixed model solved using the software DMU, each SNP being analysed individually. In other words, a genome-wide association study (GWAS)

for fillet colour was performed. The dependent variable was the astaxanthin content in muscle, derived as described above. The linear mixed model was an animal model containing the fixed effect of the animal's sex, the fixed regression on the animal's round weight (weight before slaughter), and the random regression on the number of copies of allele A carried by the animal (allele A being one of the two alleles present at the SNP).

Some DNA polymorphisms were shared by all four datasets, while others were shared by two datasets or by none. More specifically, 2,724 DNA polymorphisms were shared by all four datasets, while 1,771 DNA polymorphisms were shared by only two datasets. For DNA polymorphisms that were informative in more than one data set, an overall test statistic was produced by summing up the (chi-square distributed) test statistics from individual tests. The overall test statistics were chi-square distributed with degrees of freedom equal to the number of data sets that the overall statistic was derived from.

FIGS. 1a-1d displays Manhattan plot corresponding to the GWAS performed on Sample Sets 1, 2, 3, and 4. As can be seen in FIGS. 1a-1d, one or more DNA polymorphisms from chromosome2 were found to be strongly associated to fillet colour in each of the four data sets. In each of Data Sets 1 and 2, one DNA polymorphism from chromosome 2 was found to be experiment-wide significant, while in each of Data Sets 3 and 4, one DNA polymorphism was found to be close to experiment-wide significant. Taken together, the results prove the existence of a quantitative trait locus (QTL) for fillet colour (the ability to utilise dietary astaxanthin) on chromosome 2. Of the DNA polymorphisms that were located on chromosome 2 while being significantly associated to fillet colour in one or more data set, one particular DNA polymorphism had the most significant overall test statistic. This DNA polymorphism had identifier rs159406379 in the dbSNP database (a partition of the GenBank database), and its genomic position corresponded to position 71,437,050 within the publicly available reference sequence for Atlantic salmon chromosome 2 (GenBank identifier: NC_027301.1). rs159406379 is the subject of a co-pending patent application, ie International Patent Application No. PCT/GB2015/051713 (wholly incorporated herein by reference). The sequence of the DNA polymorphism (with flanking sequences) was TAAATGACCTGG-TACAACAGCAAAATGAACTAAACGGAAACATCT-GCTAA[A/C] TACTT TAATTATTGCAAATGCTC- AG-GCAGCTGCATTTTCTGTTATGAAAG (SEQ ID NO:6 (A allele) and SEQ ID NO:7 (C allele)), with the C (cytosine) allele being correlated to a greater than normal ability to utilise dietary pigment, and the A (adenine) allele corresponding to a lesser than normal ability to utilise dietary pigment For most polymorphic loci (in any species), there will be a number of other loci having identical or highly similar genotype patterns. In genetic terms, two such loci will be said to be in linkage disequilibrium (LD) with each other. The squared correlation between alleles at the two loci, $r^2$, is the most commonly used measure of LD. The $r^2$ value reflects how well genotypes at one locus can predict genotypes at another locus. Thus, if locus A is capable of predicting the ability to utilise astaxhantin, and the correlation ($r^2$) between A and a second locus, locus B, is 1.0, then locus B is an equally good predictor of the utilise astaxhantin as locus A. On this background, we set out to identify additional DNA polymorphisms on chromosome 2, being in high enough LD with rs159406379. Here, high enough LD was defined as any LD value above 0.3; it is common practice among geneticists to assume $r^2$ values of 0.3 (see e.g. Uimari et al. 2005) as lower limits for 'useful LD'; the amount of LD needed if one locus is to be used as indirect indicator of another.

Additional DNA polymorphisms, in 'strong enough' ($r^2$ 0.3) with rs159406379 were identified as follows: 54 random Atlantic salmon originating from the same population from which Sample Sets 1, 2, 3, and 4 were derived, were whole-genome sequenced on Illumina HighSeq 2000, producing paired-end reads to an average genome coverage of 18× (range 8× to 32×, assuming a genome size of 3.0 billion base pairs). The reads were aligned to the reference sequence of chromosome 2 of Atlantic salmon (GenBank identifier=NC_027301.1) using BWA mem version 0.7.10-r789 (Li and Durbin 2009). SNPs and short indels were identified using Freebayes version 0.9.15-1 (Garrison and Marth 2012); to filter away low-quality variants, using run-time parameters-use-mapping-quality and -min-mapping-quality 1, in addition to 'vcffilter -f "QUAL>20"'. The SNP-detection process also returned genotypes on the 54 animals, for all identified DNA polymorphisms. SNPs and short indels were annotated using snpEff version 4.0e (Cingolani et al. 2012). The snpEff annotation database was based on the CIGENE annotation version 2.0 (Lien et al., submitted). DNA polymorphisms in sufficiently strong LD with rs159406379 were identified by running the computer program PLINK v1.9 (Chang et al. 2015) (options -r2-ld-snp rs159406379-chr-set 29-no-xy-ld-window 999999999-ld-window-kb 500). The DNA polymorphism that was found to be in strongest LD with rs159406379 (r2=0.752785) was located 32,724 bp upstream of rs159406379. More precisely, the SNP was located at position 71,404,326 within the chromosome sequence (NC_027301.1) and will hereafter be referred to as NC_ 027301.1 _71404326. Surprisingly, NC_027301.1 _71404326 was found to cause an asparagine (corresponding to a greater than normal ability to utilise dietary pigment) to serine (corresponding to a lesser than normal ability to utilise dietary pigment) amino-acid shift within the protein ATP-binding cassette transporter subfamily G member 2b. Proteins of the Abcg family are transmembrane proteins responsible for transporting compounds (preferably lipophilic compounds) from enterocytes (intestinal absorptive cells) into the lumen. The amino-acid affected by NC_027301.1 _71404326 is located within the P-loop NTPase domain of the Abcg2 protein, shown to be involved in membrane transport (Pathak and Mitsha, 2013, 2014). Thus, Abcg2 is a plausible, but far from obvious, candidate for being involved in controlling levels of astaxhantin.

Figure 2:
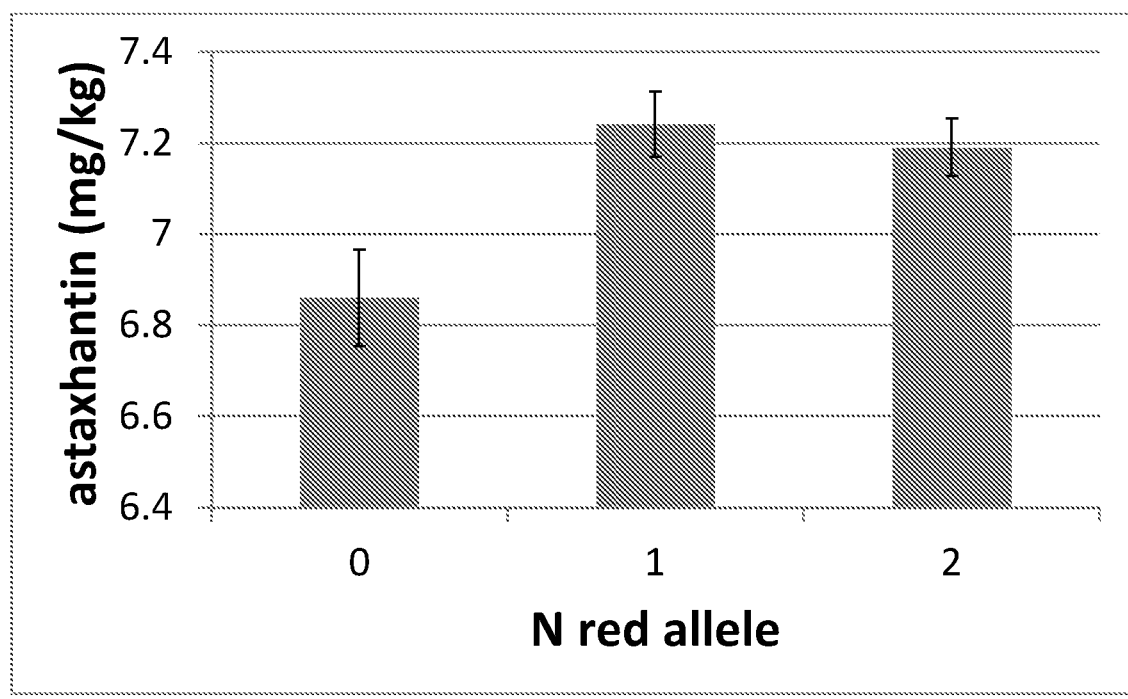
FIG. 2 displays astaxhantin levels (mg astaxhantin per kg muscle, ±standard error of the mean) in 995 Atlantic salmon individuals, the individuals having been grouped according to the genotype of one of their parents at DNA polymorphism No. 1. The x-axis indicates the number of copies of red allele in a parent (the other parent being random). Results for fish with one parent having 0, 1 or 2 copies of SNP No. 1 are shown.

In 995 animals that were offspring of at least one of the 54 Atlantic salmon having sequence-derived genotypes at NC_027301.1 _71404326, there was a significant correlation between parental genotypes at NC_027301.1 _ 71404326 and astaxhantin content in the muscle of offspring (p-value=0.037, regression of parental genotype on offspring's astaxhantin level; offspring who had both parents among the set of 54 had two data points, one per parent). As can be seen in from FIG. 2, offspring of parents having one or two copies of the red allele had significantly higher pigment levels than offspring of parents having no copies of the red allele.

Figure 3:
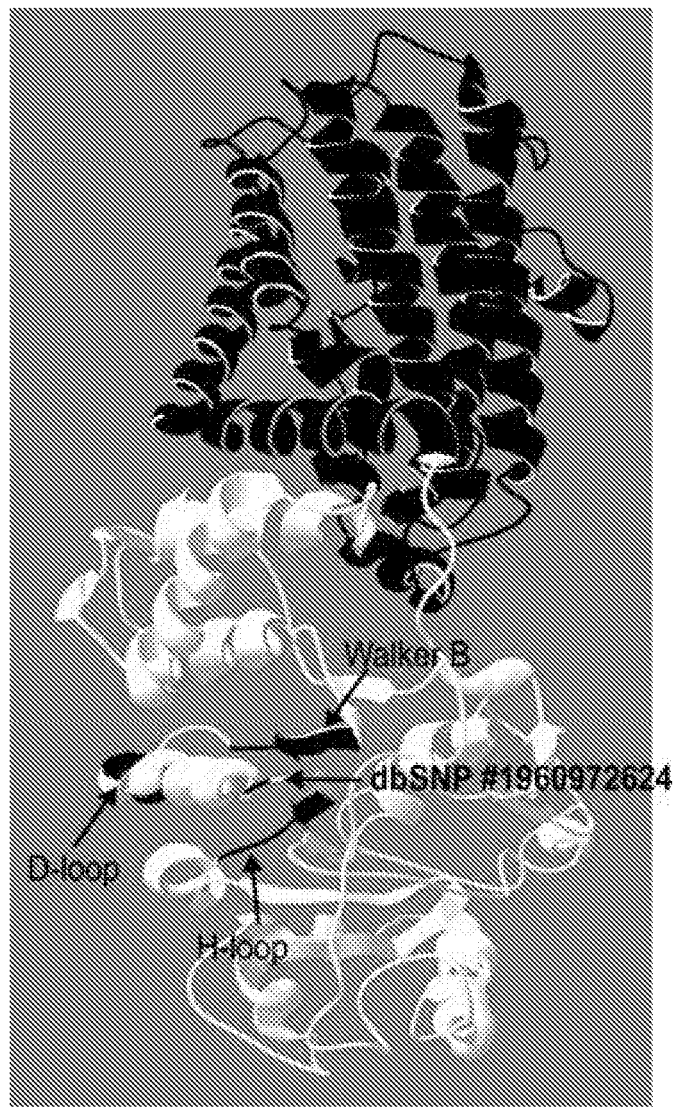
FIG. 3 displays predicted 3D protein structure of Atlantic salmon Abcg2b and dbSNP#1960972624 neighbouring domains. The intracellular nucleotide-binding domain and extracellular/transmembrane regions are coloured white and black respectively.

Considering the association between NC_027301.1 _ 71404326 and astaxhantin level, and the different properties of the Abcg2 proteins corresponding to different alleles at NC_027301.1 _71404326, NC_027301.1 _71404326 emerges as a highly probably candidate for being the causal mutation underlying the observed QTL for fillet astaxhantin content on chromosome 2. The hypothesis is backed up by the following finding: Analysis of the Abcg2b protein showed that the asparagine/serine amino acid encoded by SNP No. 1 locates to the nucleotide-binding domain of Abcg2, next to the H-loop region (FIG. 3). Mutagenesis of human Abcg2 has confirmed that amino acid shifts in the H-loop domain may impair Abcg2 transport activity (Tamura et al., 2006). The inventors carried out a MuPro (Cheng et al., 2006) SNP effect analysis on Abcg2b, and found that the replacement of serine (corresponding to pale salmon fillet) with asparagine (corresponding to red salmon fillet) decrease Abcg2 protein stability.

In order to prove the ability of SNP No. 1 to predict the ability to utilise dietary pigment, SNP No.1 was genotyped in Sample Set 1, using the iPlex genotyping system from Agena Bioscience (San Diego, USA). The details of iPlex genotyping were as follows: DNA oligonucleotides for genotypes were designed using Assay Design Suite 2.0 from Agena Bioscience (https://www.agenacx.com/Tools). The three required oligonucleotides, forward PCR primer, reverse PCR primer, and primer extension primers, had sequences ACGTTGGATGGCGGCTGAAGATTGAG-TAAC (SEQ ID NO:8), ACGTTGGATGTGTGTGTGT-GTCAGGCTGT (SEQ ID NO:9), and GGGTTGTCAG-GCTGTCTAGAA (SEQ ID NO:10) respectively. iPlex genotyping was performed according to the iPlex protocol provided by Agena Bioscience. Genotypes at NC_027-301.1 _71404326 were tested for their association to fillet colour, using DMU: The dependent variable in this analysis was the astaxanthin content in muscle, derived as described above. A linear mixed model was used, being an animal model containing the fixed effect of the animal's sex, the fixed regression on the animal's round weight (weight before slaughter), and the random regression on the number of copies of allele A carried by the animal (allele A being one of the two alleles present at NC_027301.1 _71404326). The p-value of the regression of NC_027301.1 _71404326 on fillet colour had p-value $5.33\times10^{-14}$. The mean fillet colour levels (mg astaxhantin/kg muscle, ±standard error) of individuals that were homozygous for the pale allele (cytosine), heterozygous, and homozygous for the red allele (thymine) were, respectively, 6.66±0.08, 6.88±0.04, and 7.09±0.04, respectively. NC_027301.1 _71404326 was more strongly associated to fillet colour than any other DNA polymorphism located on chromosome 2, supporting the hypothesis of NC_027301.1 _71404326 being the causative DNA polymorphism underlying the fillet colour QTL on chromosome 2.

TABLE 2

DNA polymorphism capable of determining the ability to utilise dietary pigment in Atlantic salmon, while being located within an exon or intron of abcg2.

| DNA poly-morphism No. | DNA polymorphism | dbSNP identifier (ss #) | red allele | pale allele |
|---|---|---|---|---|
| 1 | NC_027301.1_71404326 | 1960972624 | T | C |

DNA polymorphism = identifier assigned by the Inventors, consisting of the GenBank identifier of the DNA sequence of Atlantic salmon chromosome 2 (NC_027301.1) and the position of the DNA polymorphism within that sequence (71404326);
dbSNP identifier = identifiers by the dbSNP partition of the GenBank database;
red allele = allele conferring a greater than normal ability to utilise dietary pigment;
pale allele = allele conferring a lesser than normal ability to utilise dietary pigment.

TABLE 3

Sequence of a DNA polymorphism of the Invention.
The read direction of the sequence is the same as
the read direction of the reference sequence for
Atlantic salmon chromosome 2 (GenBank identifier:
NC_027301.1). The alleles are given in order [red
allele/pale allele]. The position of the SNP
within each nucleic acid sequence has been
underlined and put in bold font.
SEQ ID NO: 4 and SEQ ID NO: 5 are read in
the opposite direction that of SEQ ID NO: 1.

| DNA poly-morphism No. | Name and sequence |
|---|---|
| 1 | NC_027301.1_71404326:<br>SEQ ID NO: 4:-<br>5'GTAACGAGGCTGATGGATGGAGAAGACGATAGTCTT<br>ACCGTTTCTAGACAGCCTGACACACACACACACACACA<br>CACACAC3'<br><br>SEQ ID NO: 5:-<br>5'GTAACGAGGCTGATGGATGGAGAAGACGATAGTCTT<br>ACCGCTTCTAGACAGCCTGACACACACACACACACACA<br>CACACAC3' |

REFERENCES

Baldán A, Tarr P, Lee R, and Edwards P A (2006) ATP-binding cassette transporter G1 and lipid homeostasis. Curr Opin Lipidol. 17:227-32.

Chang C C, Chow C C, Tellier LCAM, Vattikuti S, Purcell S M, and Lee JJ (2015) Second-generation PLINK: rising to the challenge of larger and richer datasets. Gigascience, 4:7 .

Cingolani P, Platts A, Wang LL, Coon M, Nguyen T, Wang, Land SJ, Ruden DM, and Lu X (2012) A program for annotating and predicting the effects of single nucleotide polymorphisms, SnpEff: SNPs in the genome of *Drosophila melanogaster* strain w1118; iso-2; iso-3. Fly 6:2 .

Davidson WS, Koop BF, Jones SJM, Iturra P, Vidal R. et al. (2010) Sequencing the genome of the Atlantic salmon (Salmo salar). Genome Biology 11: 403.

Ferrucci L, Perry JRB, Matteini A, Perola M, Tanaka T et al. (2009) Common variation in the beta-carotene 15, 15'-monooxygenase 1 gene affects circulating levels of carotenoids: A genome-wide association study. American Journal of Human Genetics 84: 123-133 .

Garrison E and Marth G (2012) Haplotype-based variant detection from short-read sequencing. arXiv: 1207.3907v2 [q-bio.GN]

Hendrickson SJ, Hazra A, Chen C, Eliassen AH, Kraft P et al.(2012) β-Carotene 15,15'-monooxygenase 1 single nucleotide polymorphisms in relation to plasma carotenoid and retinol concentrations in women of European descent. American Journal of Clinical Nutrition 96:1379-1389 .

Industry Standards for Fish (1999) Standard for quality grading of farmed salmon, Industry standard NBS 10-01; http://fhl.nsp01cp.nhosp.no/files/Quality_grading_of_farmed_salmon.pdf Jlali M, Graulet B, Chauveau-Duriot B, Chabault M, Godet E et al. (2012) A mutation in the promoter of the chicken β,β-carotene 15,15'-monooxygenase 1 gene alters xanthophyll metabolism through a selective effect on its mRNA abundance in the breast muscle. Journal of Animal Science 90:4280-4288 .

Le Bihan-Duval E, Nadaf J, Berri C, Pitel F, Graulet B et al. (2011) Detection of a cis eQTL controlling BCMO1 gene expression leads to the identification of a QTG for chicken breast meat color. Plos One 6.

Li H and Durbin R (2009) Fast and accurate short read alignment with Burrows-Wheeler Transform. Bioinformatics 25: 1754-60.

Lien S, Gidskehaug L, Moen T, Hayes BJ, Berg PR, Davidson WS et al. (2011) A dense SNP-based linkage map for Atlantic salmon (Salmo salar) reveals extended chromosome homeologies and striking differences in sex-specific recombination patterns. BMC Genomics 12: 615.

Lietz G, Lange J, and Rimbach G (2010) Molecular and dietary regulation of beta,beta-carotene 15,15'-monooxygenase 1 (BCM1). Archives of Biochemistry and Biophysics 502:8-16.

Moen T, Baranski M, Sonesson AK, Kjøglum S (2009) Confirmation and fine-mapping of a major QTL for resistance to infectious pancreatic necrosis in Atlantic salmon (Salmo salar): population-level associations between markers and trait.

Pathak E, Mishra R (2013) Role of highly central residues of P-loop and its flanking region in preserving the archetypal conformation of Walker A motif of diverse P-loop NTPases. Bioinformation 9:23-28

Pathak E, Mishra R (2014) Analysis of P-Loop and its Flanking Region Subsequence of Diverse NTPases Reveals Evolutionary Selected Residues. Bioinformation 23:216-220.

Telbisz Á, Özvegy-Laczka C, Hegedűs T, Váradi A, and Sarkadi B. (2013) Effects of the lipid environment, cholesterol and bile acids on the function of the purified and reconstituted human ABCG2 protein. Biochem J. 450:387-95.

Uimari P, Kontkanen O, Visscher PM, Pirskanen M, Fuentes R, and Salonen JT (2005) Genome-wide linkage disequilibrium from 100,000 SNPs in the East Finland Founder population. Twin Research and Human Genetics 8: 185-197.

The invention claimed is:

1. A method of detecting one or more DNA polymorphism in the abcg2 gene in a salmon comprising:
   a) obtaining a nucleic acid sample from a salmon;
   b) assaying the nucleic acid sample for a DNA polymorphism in the abcg2 gene; and
   c) detecting the presence of a cytosine at nucleotide position 41 in SEQ ID NO. 5.

2. A method of breeding salmon, the method comprising:
   a) obtaining a nucleic acid sample from a salmon;
   b) assaying the nucleic acid sample for a DNA polymorphism in the abcg2 gene;
   c) detecting the presence of a thymine at nucleotide position 41 in SEQ ID NO. 4; and
   d) breeding from the salmon.

3. A method of breeding salmon, the method comprising breeding from a salmon, wherein the salmon has a thymine at position 41 in SEQ ID NO. 4; and
   wherein a sample from the salmon has been tested to detect the presence of a thymine at nucleotide position 41 in SEQ ID NO. 4.

4. A method of detecting one or more variants in an Abcg2 protein comprising:
   a) obtaining a sample from a salmon;
   b) assaying the sample for a variant in the Abcg2 protein; and c) detecting the presence of a serine at amino acid position 230 in SEQ ID NO. 3.

5. A method of breeding salmon, the method comprising:
a) obtaining a sample from a salmon;
b) assaying the sample for a variant in the Abcg2 protein; and
c) detecting the presence of an asparagine at amino acid position 230 in SEQ ID NO. 2; and
d) breeding from the salmon.

6. A method of breeding salmon, the method comprising breeding from a salmon, wherein the salmon has an asparagine at position 230 in SEQ ID NO. 2; and
wherein a sample from the salmon has been tested to detect the presence of a asparagine at amino acid position 230 in SEQ ID NO. 2.

* * * * *

SEQUENCE LISTING

<160> NUMBER OF SEQ ID NOS: 10

<210> SEQ ID NO 1
<211> LENGTH: 2445
<212> TYPE: DNA
<213> ORGANISM: Salmo salar

<400> SEQUENCE: 1

```
tctctctctc tccttctccc tctttctgtg aggaggatgt ctaagcccca gaatggtgag      60
ccaggcagcc cagcaggagt cccagcagca gatgatccag aggtgatgtt ccaggtgcct     120
ggtccaaccg tctccttctc cagactacac tactctgtca tggagagcaa tggactctgc     180
cacaagagag aaactgagaa acacatcctc aaagacgtta gcggcatcat gagaccaggg     240
atgaacgcca tcatggggcc aacaggaagt ggaaaaacat ctctcctgga tgtgatagca     300
ggtcgtaagg acccagcagg gttgaagttt ggtcaggttc tggtcgatgg aagatggtg      360 gactctgacc tccgactcat atctgcctac gtggtgcagg atgatatatt gatgggaacc     420
ctgtcagtga gagagaactt gttgttcagt gtgaacctga gactagaccc tagacattat     480
tgtacagctg acaaacagca gagagtagac agcatcatag aagacctggg actacaggac     540
tgtgcccaca ccaagatagg aacagagttc ctgcgtggtg tgtctggggg agagaggaag     600
aggtgcagca tcggtatgga gctgattact tctccttctc ttctgttcct ggatgaaccc     660
accactggtc tggactctaa cactgctaac catatcatca agctgctgca taggctgtct     720
agaarcggta agactatcgt cttctccatc catcagcctc gttactcaat cttcagccgc     780
tttgaccacc tgacctgat gcaccgagga gagttggtgt atgctggagc tgccgggaag     840
gccctgagct acttcactga cctggggtat cactgtgagc cgttcaacaa cccatctgac     900
ttcttcctag acatcactaa cggagaggct cagtctacac tggacatcac ttcatttaac     960
tatgaggaga actgtgacaa cagcaaccct ctggcagtga gctacagaca gtcggctcag    1020
taccagaggg tggtggagga gctggaccat ttgacccagg gtctggaggg aggggttgga    1080
ggtcagggac agaaggccga ctacgtcacc tccttctggt accagataag gatagtgtgt    1140
ggtcgtacgg tgatgaactc tctcaggaac ccccagacat cgtacgctca gcttgcccct    1200
aacatcttct tcgctctgct ggtcggcctc atctactacc agatccccct gactctacct    1260
gaagccctac agaacaggat gggagcattc tttttcctca tcatcaacat ggtgtttggg    1320
aatctttcag ctgtggaact cttcatcaat gagagagctc tgttcatcca tgagaactct    1380
```

```
agtgggtact accgtacgtc cgtctacttc ctgtctaaga tattcgctga cctcatcccc    1440
aaccgcattg tacctatctt catcttctca gccatcgcct actatatgat gggtctgaag    1500
ccagccgtca cagcgttcct gctctttgcg ctgacgatgt ccctggtcag tctagctggg    1560
gtcagtctag cgttcctggt atcagcctct gtctcctcct tcgctatggc caacgtcctc    1620
atcgcgctgc ctttcgtctt catgatggtg tttggagggt tcctggtcaa ccttaactcc    1680
atgttgtcct ggctgtcatg gctgaaatgg atcagcatct tccgctacgg cctagaggct    1740
gtgaccatca atgagtttaa aggacagata ttctacagca acacaaccat tcttccaggg    1800
gaggtgtacc tggagaccca gggaatagac tacagcacct gggggtttctg cagaaccat    1860 gtagctctgg gtgggatcat tacggtgtgt atggtcttgg cctacataca gctcagacgg    1920
atcaaccgct ggaagtaaca catgaaacta caccttctgg aacaacaggg actgtgaaga    1980
gacacacacc acaggcacac acgcacgcaa gcacacgcac tctccactct agtacattgt    2040
aatattgttg tatggttgta ttgtacattt tgtgttgtag aaatgtagtg gtgtaataat    2100
gttatatgat gtgctgttga tcttgttttt tggtgcctta atacagtcta agtcctgtct    2160
atgccggggg agggggttcta ctgaactata tggaattgtt ttaacaaggt cataccaagg    2220 atcttttttgt tatttgattt agaattttaa gactccttga ggcaatatat aaaacaaata    2280
tttgatgaac atttttattt ggccttactg ctgttaaccc atagaaacac attgaataac    2340
agattcacta cgtggaacaa cagacagtcc cagaacaaaa tgtaaaggaa gtctgatgtg    2400
tctgtcctat atctgagaga taaaagaaac atatggaaaa aaaaa                    2445
```

<210> SEQ ID NO 2
<211> LENGTH: 633
<212> TYPE: PRT
<213> ORGANISM: Salmo salar

<400> SEQUENCE: 2

```
Met Ser Lys Pro Gln Asn Gly Glu Pro Gly Ser Pro Ala Gly Val Pro
1               5                   10                  15

Ala Ala Asp Asp Pro Glu Val Met Phe Gln Val Pro Gly Pro Thr Val
            20                  25                  30

Ser Phe Ser Arg Leu His Tyr Ser Val Met Glu Ser Asn Gly Leu Cys
        35                  40                  45

His Lys Arg Glu Thr Glu Lys His Ile Leu Lys Asp Val Ser Gly Ile
    50                  55                  60

Met Arg Pro Gly Met Asn Ala Ile Met Gly Pro Thr Gly Ser Gly Lys
65                  70                  75                  80

Thr Ser Leu Leu Asp Val Ile Ala Gly Arg Lys Asp Pro Ala Gly Leu
                85                  90                  95

Lys Phe Gly Gln Val Leu Val Asp Gly Lys Met Val Asp Ser Asp Leu
            100                 105                 110

Arg Leu Ile Ser Ala Tyr Val Val Gln Asp Asp Ile Leu Met Gly Thr
        115                 120                 125

Leu Ser Val Arg Glu Asn Leu Leu Phe Ser Val Asn Leu Arg Leu Asp
    130                 135                 140

Pro Arg His Tyr Cys Thr Ala Asp Lys Gln Gln Arg Val Asp Ser Ile
145                 150                 155                 160

Ile Glu Asp Leu Gly Leu Gln Asp Cys Ala His Thr Lys Ile Gly Thr
                165                 170                 175

Glu Phe Leu Arg Gly Val Ser Gly Gly Glu Arg Lys Arg Cys Ser Ile
```

```
                    180                 185                 190
Gly Met Glu Leu Ile Thr Ser Pro Ser Leu Leu Phe Leu Asp Glu Pro
            195                 200                 205
Thr Thr Gly Leu Asp Ser Asn Thr Ala Asn His Ile Ile Lys Leu Leu
        210                 215                 220
His Arg Leu Ser Arg Asn Gly Lys Thr Ile Val Phe Ser Ile His Gln
225                 230                 235                 240
Pro Arg Tyr Ser Ile Phe Ser Arg Phe Asp His Leu Thr Leu Met His
                245                 250                 255
Arg Gly Glu Leu Val Tyr Ala Gly Ala Gly Lys Ala Leu Ser Tyr
            260                 265                 270
Phe Thr Asp Leu Gly Tyr His Cys Glu Pro Phe Asn Asn Pro Ser Asp
        275                 280                 285
Phe Phe Leu Asp Ile Thr Asn Gly Glu Ala Gln Ser Thr Leu Asp Ile
    290                 295                 300
Thr Ser Phe Asn Tyr Glu Glu Asn Cys Asp Asn Ser Asn Leu Leu Ala
305                 310                 315                 320
Val Ser Tyr Arg Gln Ser Ala Gln Tyr Gln Arg Val Val Glu Glu Leu
                325                 330                 335
Asp His Leu Thr Gln Gly Leu Glu Gly Val Gly Gln Gly Gln
            340                 345                 350
Lys Ala Asp Tyr Val Thr Ser Phe Trp Tyr Gln Ile Arg Ile Val Cys
        355                 360                 365
Gly Arg Thr Val Met Asn Ser Leu Arg Asn Pro Gln Thr Ser Tyr Ala
    370                 375                 380
Gln Leu Ala Leu Asn Ile Phe Phe Ala Leu Leu Val Gly Leu Ile Tyr
385                 390                 395                 400
Tyr Gln Ile Pro Leu Thr Leu Pro Glu Ala Leu Gln Asn Arg Met Gly
                405                 410                 415
Ala Phe Phe Phe Leu Ile Ile Asn Met Val Phe Gly Asn Leu Ser Ala
            420                 425                 430
Val Glu Leu Phe Ile Asn Glu Arg Ala Leu Phe Ile His Glu Asn Ser
        435                 440                 445
Ser Gly Tyr Tyr Arg Thr Ser Val Tyr Phe Leu Ser Lys Ile Phe Ala
    450                 455                 460
Asp Leu Ile Pro Asn Arg Ile Val Pro Ile Phe Ile Phe Ser Ala Ile
465                 470                 475                 480
Ala Tyr Tyr Met Met Gly Leu Lys Pro Ala Val Thr Ala Phe Leu Leu
                485                 490                 495
Phe Ala Leu Thr Met Ser Leu Val Ser Leu Ala Gly Val Ser Leu Ala
            500                 505                 510
Phe Leu Val Ser Ala Ser Val Ser Phe Ala Met Ala Asn Val Leu
        515                 520                 525
Ile Ala Leu Pro Phe Val Phe Met Met Val Phe Gly Gly Phe Leu Val
    530                 535                 540
Asn Leu Asn Ser Met Leu Ser Trp Leu Ser Trp Leu Lys Trp Ile Ser
545                 550                 555                 560
Ile Phe Arg Tyr Gly Leu Glu Ala Val Thr Ile Asn Glu Phe Lys Gly
                565                 570                 575
Gln Ile Phe Tyr Ser Asn Thr Thr Ile Leu Pro Gly Glu Val Tyr Leu
            580                 585                 590
Glu Thr Gln Gly Ile Asp Tyr Ser Thr Trp Gly Phe Trp Gln Asn His
        595                 600                 605
```

```
Val Ala Leu Gly Gly Ile Ile Thr Val Cys Met Val Leu Ala Tyr Ile
    610                 615                 620

Gln Leu Arg Arg Ile Asn Arg Trp Lys
625                 630
```

<210> SEQ ID NO 3
<211> LENGTH: 633
<212> TYPE: PRT
<213> ORGANISM: Salmo salar

<400> SEQUENCE: 3

```
Met Ser Lys Pro Gln Asn Gly Glu Pro Gly Ser Pro Ala Gly Val Pro
1               5                   10                  15

Ala Ala Asp Asp Pro Glu Val Met Phe Gln Val Pro Gly Pro Thr Val
            20                  25                  30

Ser Phe Ser Arg Leu His Tyr Ser Val Met Glu Ser Asn Gly Leu Cys
        35                  40                  45

His Lys Arg Glu Thr Glu Lys His Ile Leu Lys Asp Val Ser Gly Ile
    50                  55                  60

Met Arg Pro Gly Met Asn Ala Ile Met Gly Pro Thr Gly Ser Gly Lys
65                  70                  75                  80

Thr Ser Leu Leu Asp Val Ile Ala Gly Arg Lys Asp Pro Ala Gly Leu
                85                  90                  95

Lys Phe Gly Gln Val Leu Val Asp Gly Lys Met Val Asp Ser Asp Leu
            100                 105                 110

Arg Leu Ile Ser Ala Tyr Val Val Gln Asp Asp Ile Leu Met Gly Thr
        115                 120                 125

Leu Ser Val Arg Glu Asn Leu Leu Phe Ser Val Asn Leu Arg Leu Asp
    130                 135                 140

Pro Arg His Tyr Cys Thr Ala Asp Lys Gln Gln Arg Val Asp Ser Ile
145                 150                 155                 160

Ile Glu Asp Leu Gly Leu Gln Asp Cys Ala His Thr Lys Ile Gly Thr
                165                 170                 175

Glu Phe Leu Arg Gly Val Ser Gly Gly Glu Arg Lys Arg Cys Ser Ile
            180                 185                 190

Gly Met Glu Leu Ile Thr Ser Pro Ser Leu Leu Phe Leu Asp Glu Pro
        195                 200                 205

Thr Thr Gly Leu Asp Ser Asn Thr Ala Asn His Ile Ile Lys Leu Leu
    210                 215                 220

His Arg Leu Ser Arg Ser Gly Lys Thr Ile Val Phe Ser Ile His Gln
225                 230                 235                 240

Pro Arg Tyr Ser Ile Phe Ser Arg Phe Asp His Leu Thr Leu Met His
                245                 250                 255

Arg Gly Glu Leu Val Tyr Ala Gly Ala Ala Gly Lys Ala Leu Ser Tyr
            260                 265                 270

Phe Thr Asp Leu Gly Tyr His Cys Glu Pro Phe Asn Asn Pro Ser Asp
        275                 280                 285

Phe Phe Leu Asp Ile Thr Asn Gly Glu Ala Gln Ser Thr Leu Asp Ile
    290                 295                 300

Thr Ser Phe Asn Tyr Glu Glu Asn Cys Asp Asn Ser Asn Leu Leu Ala
305                 310                 315                 320

Val Ser Tyr Arg Gln Ser Ala Gln Tyr Gln Arg Val Val Glu Glu Leu
                325                 330                 335

Asp His Leu Thr Gln Gly Leu Glu Gly Gly Val Gly Gly Gln Gly Gln
```

```
                340             345             350
Lys Ala Asp Tyr Val Thr Ser Phe Trp Tyr Gln Ile Arg Ile Val Cys
            355                 360                 365
Gly Arg Thr Val Met Asn Ser Leu Arg Asn Pro Gln Thr Ser Tyr Ala
            370                 375                 380
Gln Leu Ala Leu Asn Ile Phe Phe Ala Leu Leu Val Gly Leu Ile Tyr
385                 390                 395                 400
Tyr Gln Ile Pro Leu Thr Leu Pro Glu Ala Leu Gln Asn Arg Met Gly
                405                 410                 415
Ala Phe Phe Phe Leu Ile Ile Asn Met Val Phe Gly Asn Leu Ser Ala
                420                 425                 430
Val Glu Leu Phe Ile Asn Glu Arg Ala Leu Phe Ile His Glu Asn Ser
            435                 440                 445
Ser Gly Tyr Tyr Arg Thr Ser Val Tyr Phe Leu Ser Lys Ile Phe Ala
            450                 455                 460
Asp Leu Ile Pro Asn Arg Ile Val Pro Ile Phe Ile Phe Ser Ala Ile
465                 470                 475                 480
Ala Tyr Tyr Met Met Gly Leu Lys Pro Ala Val Thr Ala Phe Leu Leu
                485                 490                 495
Phe Ala Leu Thr Met Ser Leu Val Ser Leu Ala Gly Val Ser Leu Ala
                500                 505                 510
Phe Leu Val Ser Ala Ser Val Ser Ser Phe Ala Met Ala Asn Val Leu
            515                 520                 525
Ile Ala Leu Pro Phe Val Phe Met Met Val Phe Gly Gly Phe Leu Val
            530                 535                 540
Asn Leu Asn Ser Met Leu Ser Trp Leu Ser Trp Leu Lys Trp Ile Ser
545                 550                 555                 560
Ile Phe Arg Tyr Gly Leu Glu Ala Val Thr Ile Asn Glu Phe Lys Gly
                565                 570                 575
Gln Ile Phe Tyr Ser Asn Thr Thr Ile Leu Pro Gly Glu Val Tyr Leu
                580                 585                 590
Glu Thr Gln Gly Ile Asp Tyr Ser Thr Trp Gly Phe Trp Gln Asn His
            595                 600                 605
Val Ala Leu Gly Gly Ile Ile Thr Val Cys Met Val Leu Ala Tyr Ile
            610                 615                 620
Gln Leu Arg Arg Ile Asn Arg Trp Lys
625                 630

<210> SEQ ID NO 4
<211> LENGTH: 81
<212> TYPE: DNA
<213> ORGANISM: Salmo salar

<400> SEQUENCE: 4
gtaacgaggc tgatggatgg agaagacgat agtcttaccg tttctagaca gcctgacaca    60
cacacacaca cacacacaca c                                              81

<210> SEQ ID NO 5
<211> LENGTH: 81
<212> TYPE: DNA
<213> ORGANISM: Salmo salar

<400> SEQUENCE: 5
gtaacgaggc tgatggatgg agaagacgat agtcttaccg cttctagaca gcctgacaca    60
cacacacaca cacacacaca c                                              81
```

```
<210> SEQ ID NO 6
<211> LENGTH: 101
<212> TYPE: DNA
<213> ORGANISM: Salmo salar

<400> SEQUENCE: 6
taaatgacct ggtacaacag caaaatgaac taaacggaaa catctgctaa atactttaat    60
tattgcaaat gctcaggcag ctgcattttc tgttatgaaa g                        101

<210> SEQ ID NO 7
<211> LENGTH: 101
<212> TYPE: DNA
<213> ORGANISM: Salmo salar

<400> SEQUENCE: 7
taaatgacct ggtacaacag caaaatgaac taaacggaaa catctgctaa ctactttaat    60
tattgcaaat gctcaggcag ctgcattttc tgttatgaaa g                        101

<210> SEQ ID NO 8
<211> LENGTH: 30
<212> TYPE: DNA
<213> ORGANISM: Artificial Sequence
<220> FEATURE:
<223> OTHER INFORMATION: Synthetic primer

<400> SEQUENCE: 8
acgttggatg gcggctgaag attgagtaac                                     30

<210> SEQ ID NO 9
<211> LENGTH: 29
<212> TYPE: DNA
<213> ORGANISM: Artificial Sequence
<220> FEATURE:
<223> OTHER INFORMATION: Synthetic primer

<400> SEQUENCE: 9
acgttggatg tgtgtgtgtg tcaggctgt                                      29

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
gggttgtcag gctgtctaga a                                              21
```